US007595640B2

(12) United States Patent
Ladebeck et al.

(10) Patent No.: US 7,595,640 B2
(45) Date of Patent: Sep. 29, 2009

(54) TOMOGRAPHIC MEASURING SYSTEM AND METHOD FOR CONDUCTING MEASUREMENTS

(75) Inventors: Ralf Ladebeck, Erlangen (DE); Georg Pirkl, Dormitz (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/007,739

(22) Filed: Jan. 15, 2008

(65) Prior Publication Data

US 2008/0169812 A1 Jul. 17, 2008

(30) Foreign Application Priority Data

Jan. 16, 2007 (DE) .................. 10 2007 002 306

(51) Int. Cl.
*G01V 3/00* (2006.01)
(52) U.S. Cl. ...................... 324/318; 324/322
(58) Field of Classification Search ............. 324/318, 324/322; 600/411
See application file for complete search history.

(56) References Cited

U.S. PATENT DOCUMENTS 6,501,978 B2* 12/2002 Wagshul et al. ............ 600/411
6,735,461 B2* 5/2004 Vitek et al. ................. 600/411
6,961,606 B2* 11/2005 DeSilets et al. ............. 600/415
7,286,867 B2* 10/2007 Schlyer et al. .............. 600/407
2006/0250133 A1 11/2006 Krieg et al.
2008/0214927 A1* 9/2008 Cherry et al. ............... 600/411

FOREIGN PATENT DOCUMENTS

DE 102005015071 A1 10/2006

\* cited by examiner

*Primary Examiner*—Louis M Arana
(74) *Attorney, Agent, or Firm*—Harness, Dickey & Pierce, P.L.C.

(57) ABSTRACT

A tomographic measuring system is disclosed with at least two tomographic measuring devices, of which at least a first can interfere with a second in a manner disadvantageous for conducting measurements. In at least one embodiment, the system includes a switching-off mechanism at least in the first measuring device; and at least one external connection to the first measuring device for transmitting a switching-off signal to the switching-off mechanism, if the second measuring device is conducting a measurement or will conduct one. A method for conducting measurements with an appropriate tomographic measuring system is also disclosed.

18 Claims, 1 Drawing Sheet

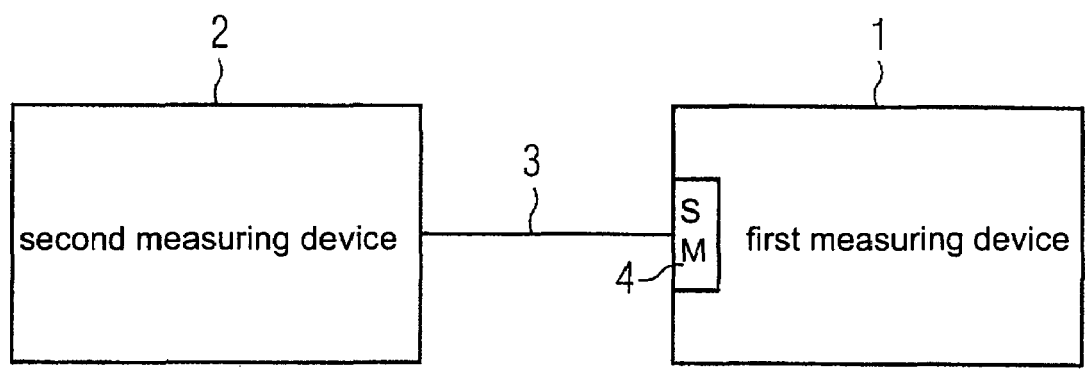

TOMOGRAPHIC MEASURING SYSTEM AND METHOD FOR CONDUCTING MEASUREMENTS

PRIORITY STATEMENT

The present application hereby claims priority under 35 U.S.C. §119 on German patent application number DE 10 2007 002 306.7 filed Jan. 16, 2007, the entire contents of which is hereby incorporated herein by reference.

FIELD

Embodiments of the present invention generally relate to a tomographic measuring system with at least two tomographic measuring devices and/or a method aimed at conducting measurements with a corresponding tomographic measuring system.

BACKGROUND

Alongside magnetic resonance tomography (MR), positron emission tomography (PET) has also become increasingly widespread of recent years in medical diagnosis. While MR tomography is an imaging method for displaying structures and slice images in the interior of the body, PET enables a visualization and quantification of metabolic activities in vivo.

PET uses the particular properties of positron emitters and positron annihilation in order to determine the function of organs or cell areas quantitatively. In this case, before the examination the patient is administered appropriate radiopharmaceuticals that are marked with radionuclides. In the event of decay, the radionuclides emit positrons that interact with an electron after a short distance, resulting in a so-called annihilation. Two gamma quanta are produced in this case and fly apart from one another in opposite directions (offset by 180°). The gamma quanta are detected by two opposite PET detector modules inside a specific time window (coincidence measurement), as a result of which the location of the annihilation is determined at a position on the connecting line between these two detector modules.

For detection, in the case of PET the detector module must generally cover a major part of the length of the gantry arc. Said module is subdivided into detector elements with a side length of a few millimeters. When detecting a gamma quantum, each detector element generates an event record that specifies the time and the detection location, that is to say the appropriate detector element. These items of information are transferred to a fast logic unit and compared. If two events coincide with a maximum time spacing, it is assumed that there is a gamma decay process on the connecting line between the two associated detector elements. The reconstruction of the PET image is performed with the aid of a tomography algorithm, that is to say the so-called back projection.

A superposed imaging of the two methods is desirable in many instances on the basis of the different items of information that are obtained by MRI and PET.

In the field of tomographic measuring methods the problem arises namely that a positron emission tomography system (PET) can only deliver functional images and not anatomical ones. Combining the imaging methods of MRI and PET into one unit and making it possible to use them simultaneously, as far as possible, is a development goal for future systems. In order to be able to undertake an assignment of the recorded functional areas to the anatomical structures, a magnetic resonance tomography unit is combined with a PET unit, generally by fitting a PET measuring device into an MR unit. However, in doing so, the problem arises that the PET measuring device must not interfere with the MR measurements and vice versa—something that can happen due to the physical principles used.

Until now it has been usual to combine the two measuring devices by design appropriate shielding of the whole system and by providing measures between the two devices. One design measure with a specific design can be, for instance, to avoid the magnetic components in the PET measuring device. One appropriate measure against the incoming and outgoing radio-frequency radiation would be an electromagnetic radiation-tight screening cover; however, the realization thereof is often difficult and/or complex, so that, in general, this is refrained from.

SUMMARY

At least one embodiment of the present application therefore arises out of making an economic approach available, with which it can be ensured that measuring devices cannot interfere with or influence one another.

At least one embodiment of the invention is directed to a tomographic measuring system and/or measuring method. Further advantageous embodiments, details and features of the present invention arise from the description.

At least one embodiment of the invention is based on the principle of ensuring in a simple fashion that a measuring device which may interfere is turned off during the measuring time of a measuring device experience interference.

Accordingly, a first aspect of at least one embodiment of the invention focuses on a tomographic measuring system, which has:

- at least two tomographic measuring devices, of which at least one can interfere with a second in a manner disadvantageous for conducting measurements,
- a switching-off mechanism at least in the first measuring device;
- at least one external connection to the first measuring device for transmitting a switching-off signal to the switching-off mechanism, if the second measuring device is conducting a measurement or will conduct one.

It is understood that the principles of at least one embodiment of the invention can be extended to a system of more than two combined measuring devices and to more than one switching-off mechanism, and also to a plurality of connections, appropriate for the needs of switching off particular measuring devices in a measuring system with a plurality of measuring devices.

It is also understood that the switching-off can be carried out reciprocally, that is to say both or all measuring devices have a switching-off mechanism and appropriate connections, it still being possible to use a bidirectional external connection which can transmit switching-off signals in both directions.

The measuring devices can have different physical acquisition principles.

One of the measuring devices can preferably be a PET tomography measuring device. One of the measuring devices can also be an MR tomography measuring device.

It is particularly preferable that one measuring device is a PET tomography device and one measuring device is an MR tomography measuring device.

Due to specific experiences with appropriate measuring systems, it is particularly preferable that the first measuring device is a PET tomography measuring device and the second measuring device is an MR tomography measuring device.

Specifically, in a typical MR measurement data is not constantly being acquired, nor are radiofrequency (RF) signals constantly being sent, rather this occurs intermittently with the following simplified measuring cycle: 1. send RF pulse, 2. wait for a period of time TE (echo time) of up to approximately 100 ms, 3. read out one or more rows of the image matrix (in k-space), 4. wait for a period of time TR (repetition time) from a few of ms up to more than 100 ms, sometimes up to 3-5 s until the repetition of step 1.

However, the PET measurement running at the same is essentially only interfered with by the RF pulse. It is thus sufficient if the PET detector, as first measuring system, is in each case switched-off only during the sending of the RF-pulse, but acquires data during steps 2 to 4. Thus, at least one embodiment of the invention enables MR and PET measurements to be conducted quasi-simultaneously, the PET detectors only being switched-off or desensitized in each case for a short period of time of up to 1 ms during the RF pulse at intervals of a few milliseconds up to approximately one second. Therefore, in this embodiment the MR tomography measuring device transmits a switching-off signal to the switching-off mechanism of the PET measuring device in each case just before an RF pulse.

In an example embodiment, the external connection is an electrical connection, whereas in another embodiment it is an optical connection.

In at least one embodiment, the external connection is attached to an output of one measuring device, which is simultaneously intended for connecting the measuring device to a further unit. In this manner, at least one embodiment of the invention is also accessible to existing systems, as long as they have an output from which an activity signal can be tapped in such a manner that it can be interpreted a switching-off signal. In such a case, and also in principle, the switching-off signal is not a specific signal, but occurs due to the operational activity of the first measuring device, virtually as a "waste product". Moreover, it is also possible to undertake an extension of the measuring device, which can, without any kind of intervention on the measuring device, acquire an onset of activity in the measuring device by external sampling of internal signals and interpreting these signals and which can, in the presence of an appropriate activity, generate a switching-off signal.

In a further example embodiment, the external connection is an optical connection and the external connection has an optical waveguide branching device, whose two split outputs are connected to the first device and the further unit. In the case of enough optical output power at the output unit, the signal can be split by such an optical waveguide branching device or optical waveguide coupler into two optical waveguide strands. The optical waveguide branching device, thus has one input and two outputs and is completely passive in this case. In an alternative embodiment, if the optical output power of the optical connection is not sufficient for splitting, the light signal is converted into an electrical signal again and subsequently output to two optical waveguide optical transmitters. This is an active coupling, which requires an additional voltage supply.

Preferably the measuring system furthermore has a feedback channel for transmitting a feedback signal to the second measuring device once the first measuring device has been switched-off. This feedback channel can physically either be the same external connection as the external connection which transmits the switching-off signal and is thus bidirectional, but it can also be a separate connection which has to additionally be established between the two measuring devices.

In a further aspect, at least one embodiment of the present invention is focused on a method for tomographic measurement, everything said about the measuring system being applicable to the method and vice versa, so that reference is made alternately.

The method for tomographic measurement with the aid of two measuring devices based on different acquisition principles, of which at least a first can interfere with a second in a manner disadvantageous for conducting measurements, has the following steps:

sending a switching-off signal to an external connection to a switching-off mechanism in the first measuring device when an instruction for measurement by the second apparatus is determined;

switching off or desensitizing the first measuring device up on arrival of the switching-off signal; and conducting the measurement by the second apparatus.

As a result of this sequential coordination of different method steps, the first measuring device is switched-off or desensitized prior to the start of the actual measurement, or at the latest with the start of the measurement, so that it can no longer interfere with the measurement by the second apparatus, and that the measurement is conducted in the second apparatus only after the switching-off.

In this case, as well, one of the measuring apparatuses can be a PET tomography measuring device and one of the measuring devices can be an MR tomography measuring device. It is particularly preferred, that one measuring device is a PET tomography measuring device and one measuring device is an MR tomography measuring device.

It is particularly preferred that the first measuring device is a PET tomography measuring device and the second measuring device is an MR tomography measuring device. Here, it is also understood that the method can also be turned around, so that the first measuring device is an MR tomography measuring device and the second measuring device is a PET tomography measuring device, it being optionally possible to use a plurality of external connections or a bidirectional external connection, if the two variants of the method are to be possible with one measuring device and one method.

In an example embodiment, the method according to the invention comprises the further steps of:

sending a feedback signal to the second measuring device after switching-off or desensitization is completed;

the measurement being conducted by the second measuring device after reception of the feedback signal by the second measuring device.

It is understood that a reactivation of the first measuring unit can also take place after the measurement has been completed. This can happen either through ceasing the transmission of the switching-off signal, or through transmitting a specific reactivation signal, in which the same external connection can be used.

BRIEF DESCRIPTION OF THE DRAWINGS

The present method and the associated apparatus are explained briefly once again below with the aid of an exemplary example embodiment in conjunction with the drawings, without restricting the scope of protection prescribed by the patent claims. Here:

FIG. 1 shows the basic principle of the present invention schematically.

DETAILED DESCRIPTION OF THE EXAMPLE EMBODIMENTS

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the terms "and/or" and "at least one of" include any and all combinations of one or more of the associated listed items.

FIG. 1 shows the basic principle of the present invention schematically. A switching-off mechanism 4 attached to or in a first measuring device 1 is connected to a second measuring device 2 via an external connection 3, for example an electrical data bus, in which case if the second measuring device would like to conduct a measurement it sends a switching-off signal to the switching-off mechanism 4, which thereupon puts the first measuring device 1 into a state in which it can no longer interfere with the second measuring device 2, for example switch it off.

In particular, the advantages of an embodiment of the invention presented above are:

the switching-off signal allows the operation of a PET measuring device in an MR machine without complex shielding measures.

The switching-off signal can already be an existing control signal, such as sequence active or RF_ON or RF power amplifier unblank.

A passive optical waveguide branching device does not require an extension of the control with an additional output and also requires no additional power supply.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A tomographic measuring system, comprising:
   at least two tomographic measuring devices, where at least a first tomographic measuring device can interfere with a second tomographic measuring device in a manner disadvantageous for conducting measurements;
   a switching-off mechanism included at least in the first tomographic measuring device;
   at least one external connection to the first measuring device for transmitting a switching-off signal to the switching-off mechanism, if at least one of the second measuring device is conducting a measurement and the second measuring device will conduct a measurement; and a feedback channel for transmitting a feedback signal to the second measuring device once the first measuring device has been switched-off.

2. The measuring system as claimed in claim 1, wherein the first and second measuring devices have different acquisition principles.

3. The measuring system as claimed in claim 2, wherein one of the first and second measuring devices is a PET tomography measuring device.

4. The measuring system as claimed in claim 1, wherein one of the first and second measuring devices is a PET tomography measuring device.

5. The measuring system as claimed in claim 1, wherein one of the first and second measuring devices is an MR tomography measuring device.

6. The measuring system as claimed in claim 1, wherein one of the first and second measuring devices is a PET tomography device and one of the first and second measuring devices is an MR tomography measuring device.

7. The measuring system as claimed in claim 6, wherein the first measuring device is a PET tomography measuring device and the second measuring device is an MR tomography measuring device.

8. The measuring system as claimed in claim 1, wherein the external connection is an electrical connection.

9. The measuring system as claimed in claim 1, wherein the external connection is an optical connection.

10. The measuring system as claimed in claim 1, wherein the external connection is attached to an output of one of the first and second measuring devices, and is simultaneously intended for connecting the one of the first and second measuring devices to a further unit.

11. The measuring system as claimed in claim 1, wherein the external connection is an optical connection and the external connection has an optical waveguide branching device, where two split outputs are connected to the first measuring device and a further unit.

12. A method for tomographic measurement with the aid of two measuring devices, of which at least a first measuring device can interfere with a second measuring device in a manner disadvantageous for conducting measurements, comprising:
   sending a switching-off signal via an external connection to a switching-off mechanism in the first measuring device when an instruction for measurement by the second measuring device is determined;
   at least one of switching off and desensitizing the first measuring device upon arrival of the switching-off signal;
   sending a feedback signal to the second measuring device after switching-off or desensitization is completed; and
   conducting the measurement by the second measuring device after reception of the feedback signal by the second measuring device.

13. The method as claimed in claim 12, wherein one of the first and second measuring devices is a PET tomography measuring device.

14. The method as claimed in claim 13, wherein one of the first and second measuring devices is an MR tomography measuring device.

15. The method as claimed in claim 12, wherein one of the first and second measuring devices is an MR tomography measuring device.

16. The method as claimed in claim 12, wherein one of the first and second measuring devices is a PET tomography measuring device and one of the first and second measuring devices is an MR tomography measuring device.

17. The method as claimed in claim 16, wherein the first measuring device is a PET tomography measuring device and the second measuring device is an MR tomography measuring device.

18. A computer readable medium including program segments for, when executed on a computer device, causing the computer device to implement the method of claim 12.

* * * * *